(12) United States Patent
Whang et al.

(10) Patent No.: US 10,368,740 B2
(45) Date of Patent: Aug. 6, 2019

(54) METHOD AND SYSTEM FOR NONCONTACT VISION-BASED 3D COGNITIVE FATIGUE MEASURING BY USING TASK EVOKED PUPILLARY RESPONSE

(71) Applicants: SANGMYUNG UNIVERSITY INDUSTRY-ACADEMY COOPERATION FOUNDATION, Seoul (KR); CENTER OF HUMAN-CENTERED INTERACTION FOR COEXISTENCE, Seoul (KR)

(72) Inventors: Min Cheol Whang, Goyang-si (KR); Sang In Park, Seoul (KR); Myoung Ju Won, Cheonan-si (KR); Dong Won Lee, Seongnam-si (KR)

(73) Assignees: Sangmyung University Industry-Academy Cooperation Foundation, Seoul (KR); Center Of Human Centered Interaction For Coexistence, Seoul (KR)

( * ) Notice: Subject to any disclaimer, the term of this patent is extended or adjusted under 35 U.S.C. 154(b) by 0 days.

(21) Appl. No.: 15/869,550

(22) Filed: Jan. 12, 2018

(65) Prior Publication Data
US 2018/0220885 A1 Aug. 9, 2018

(30) Foreign Application Priority Data

Feb. 3, 2017 (KR) .................. 10-2017-0015696
Jun. 23, 2017 (KR) .................. 10-2017-0079946

(51) Int. Cl.
*A61B 3/14* (2006.01)
*A61B 3/11* (2006.01)
(Continued)

(52) U.S. Cl.
CPC .............. *A61B 3/112* (2013.01); *A61B 5/162* (2013.01); *A61B 5/163* (2017.08); *A61B 5/0452* (2013.01);
(Continued)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS

| 2002/0024633 | A1* | 2/2002 | Kim | ...................... G06T 7/0012 |
| | | | | 351/206 |
| 2011/0228224 | A1* | 9/2011 | Siminou | ................ A61B 3/112 |
| | | | | 351/206 |
| 2016/0192837 | A1* | 7/2016 | Neice | ..................... A61B 3/112 |
| | | | | 351/206 |

OTHER PUBLICATIONS

Mun et al., "SSVEP and ERP Measurement of Cognitive Fatigue Caused by Stereoscopic 3D", Neuroscience Letters, 2012, pp. 89-94, vol. 525, Elsevier Ireland Ltd.
(Continued)

*Primary Examiner* — Mohammed A Hasan
(74) *Attorney, Agent, or Firm* — Buchanan Ingersoll & Rooney PC

(57) ABSTRACT

Provided are a method and system for noncontact vision-based 3D cognitive fatigue measuring. The method comprises: acquiring pupil images of a subject exposed to visual stimuli; extracting a task evoked pupillary response (TEPR) by using the pupil images; detecting dominant peaks from the TEPR; calculating latency of dominant peaks; and determining cognitive fatigue of the subject by comparing a value of the latency to a predetermined reference value.

9 Claims, 14 Drawing Sheets

(51) Int. Cl.
  *A61B 5/16* (2006.01)
  *A61B 5/00* (2006.01)
  *A61B 5/0452* (2006.01)
  *A61B 5/0482* (2006.01)
  *A61B 5/0484* (2006.01)

(52) U.S. Cl.
  CPC ......... *A61B 5/0482* (2013.01); *A61B 5/04842* (2013.01); *A61B 5/4064* (2013.01); *A61B 5/7235* (2013.01)

(58) Field of Classification Search
  USPC ........................................................ 351/206
  See application file for complete search history.

(56) References Cited

OTHER PUBLICATIONS

Park et al., "Does Visual Fatigue from 3D Displays Affect Autonomic Regulation and Heart Rhythm", International Journal of Psychophysiology, 2014, pp. 42-48, vol. 92, Elsevier B.V.

Park et al., "Evaluation 3D Cognitive Fatigue using Heart-Brain Synchronization", International Journal of Psychophysiology, 2015, pp. 120-130, vol. 97, Elsevier B.V.

Daugman, "How Iris Recognition Works", IEEE Transactions on Circuits and Systems for Video Technology, Jan. 2004, pp. 21-30, vol. 14, No. 1, IEEE.

Lee et al., "Minimizing Eyestrain on LCD TV Based on Edge Difference and Scene Change", IEEE Transaction on Consumer Electronics, Nov. 2009, pp. 2294-2300, vol. 55, No. 4, IEEE.

Lee et al., "The Comparative Measurements of Eyestrain Caused by 2D and 3D Displays", IEEE, 2010, pp. 1677-1683.

\* cited by examiner

FIG. 14

METHOD AND SYSTEM FOR NONCONTACT VISION-BASED 3D COGNITIVE FATIGUE MEASURING BY USING TASK EVOKED PUPILLARY RESPONSE

CROSS-REFERENCE TO RELATED APPLICATION

This application claims the benefit of Korean Patent Application Nos. 10-2017-0015696, filed on Feb. 3, 2017, and 10-2017-0079946, filed on Jun. 23, 2017, in the Korean Intellectual Property Office, the disclosures of which are incorporated herein in their entirety by reference.

BACKGROUND

1. Field

One or more embodiments relate to a method and system for detecting or evaluating cognitive fatigue by using a task evoked pupillary response based on a noncontact visual mode.

2. Description of the Related Art

Viewers tend to immerse themselves more in three-dimensional (3D) content that has higher realism and dynamism than two-dimensional (2D) contents. However, this excessive immersion often leads to adverse human factors such as a visual discomfort and fatigue.

The 3D human factors may be defined with respect to viewer characteristics (age, sex, viewing position, and visual capacity), visual content (color, luminance, and contrast), viewing environment (ambient luminance, viewing distance, viewing angle, and viewing time), display (crosstalk, pseudoscopy, resolution and refresh rate), and devices (3D glass and camera setting).

These factors have been correlated with visual fatigue recovery in order to improve the 3D viewing experience. To improve viewing experience while minimizing visual fatigue, methods of quantitative measurement have been developed. 3D visual fatigue has been qualitatively measured by subjective rating while it has been quantitatively measured by cardiac response, brain function, and visual capability.

Recently, however, cognitive load has been utilized to measure 3D visual fatigue. The degradation of cognitive processing is a primary factor in visual discomfort. 3D content, having more depth qualities, demands more neural resource processes than 2D content. In general, visual fatigue occurs due to the process of focusing, which results in a reduction in neural resources. Therefore, 3D visual fatigue may be understood based on cognitive load rather than visual perception or function. Conventionally, 3D cognitive load has determined visual fatigue by analyzing event-related potential (ERP) and heartbeat evoked potential (HEP). These measurements have a limitation in practical applications since the bio-sensor must be attached to skin, which is burdensome and time consuming. Thus, it is required to develop a method and system to measure 3D visual fatigue without these disadvantages.

SUMMARY

One or more embodiments provide a method and system to evaluate noncontact 3D cognitive fatigue based on a pupillary response of human behavior involving physiological response.

Thus, one or more embodiments provide the method and system to reduce a measurement burden caused by measurement attachments.

One or more embodiments include acquiring moving images to process pupillary response from subjects and analysis of the pupillary response to evaluate 2D or 3D cognitive fatigue of the subject.

According to one or more exemplary embodiments, the method of measuring noncontact-vision-based cognitive fatigue comprises acquiring pupil images of a subject exposed to visual stimuli; extracting a task evoked pupillary response (TEPR) by using the pupil images; detecting dominant peaks from the TEPR; calculating latency of the dominant peaks; and determining cognitive fatigue of the subject by comparing a value of the latency to a predetermined reference value.

According to one or more exemplary embodiments, the acquiring of the pupil images comprises capturing face images of the subject by using a video camera; extracting pupil images from the face images; and extracting a pupil size variation (PSV) from the pupil images, and wherein the calculating comprises calculating the TEPR from the PSV.

According to one or more exemplary embodiments, the extracting of the PSV comprises resampling the face images at a predetermined frequency; and extracting the PSV from the resampled face images.

According to one or more exemplary embodiments, the method further comprising: extracting unit PSVs divided into epochs of 1200 ms based on a stimulus onset of −200 to 1000 milliseconds.

According to one or more exemplary embodiments, the TEPR is calculated or produced by combining the unit PSVs by using a grand average technique.

According to one or more exemplary embodiments, the system for measuring noncontact-vision-based cognitive fatigue, the system comprises a video camera configured to acquire pupil images of a subject exposed to visual stimuli; a processing unit configured to process the pupil images; and an analyzing unit configured to extract a task evoked pupillary response (TEPR) by using the pupil images, detect dominant peaks from the TEPR, calculate latency of dominant peaks, and determine the cognitive fatigue by comparing a value of the latency to a predetermined reference value.

According to one or more exemplary embodiments, the processing unit is further configured to extract pupil images from face images and extract a PSV from the pupil images by resampling at a predetermined sampling frequency.

According to one or more exemplary embodiments, the analyzing unit is further configured to calculate unit PSVs divided into epochs of 1200 ms based on a stimulus onset of −200 to 1000 milliseconds.

According to one or more exemplary embodiments, the analyzing unit is further configured to calculate the TEPR by combining the unit PSVs by using a grand average technique.

BRIEF DESCRIPTION OF THE DRAWINGS

These and/or other aspects will become apparent and more readily appreciated from the following description of the embodiments, taken in conjunction with the accompanying drawings in which:

FIG. 14 shows a multi-trait and multi-method (MTMM) matrix according to an exemplary embodiment.

DETAILED DESCRIPTION

Figure 1:
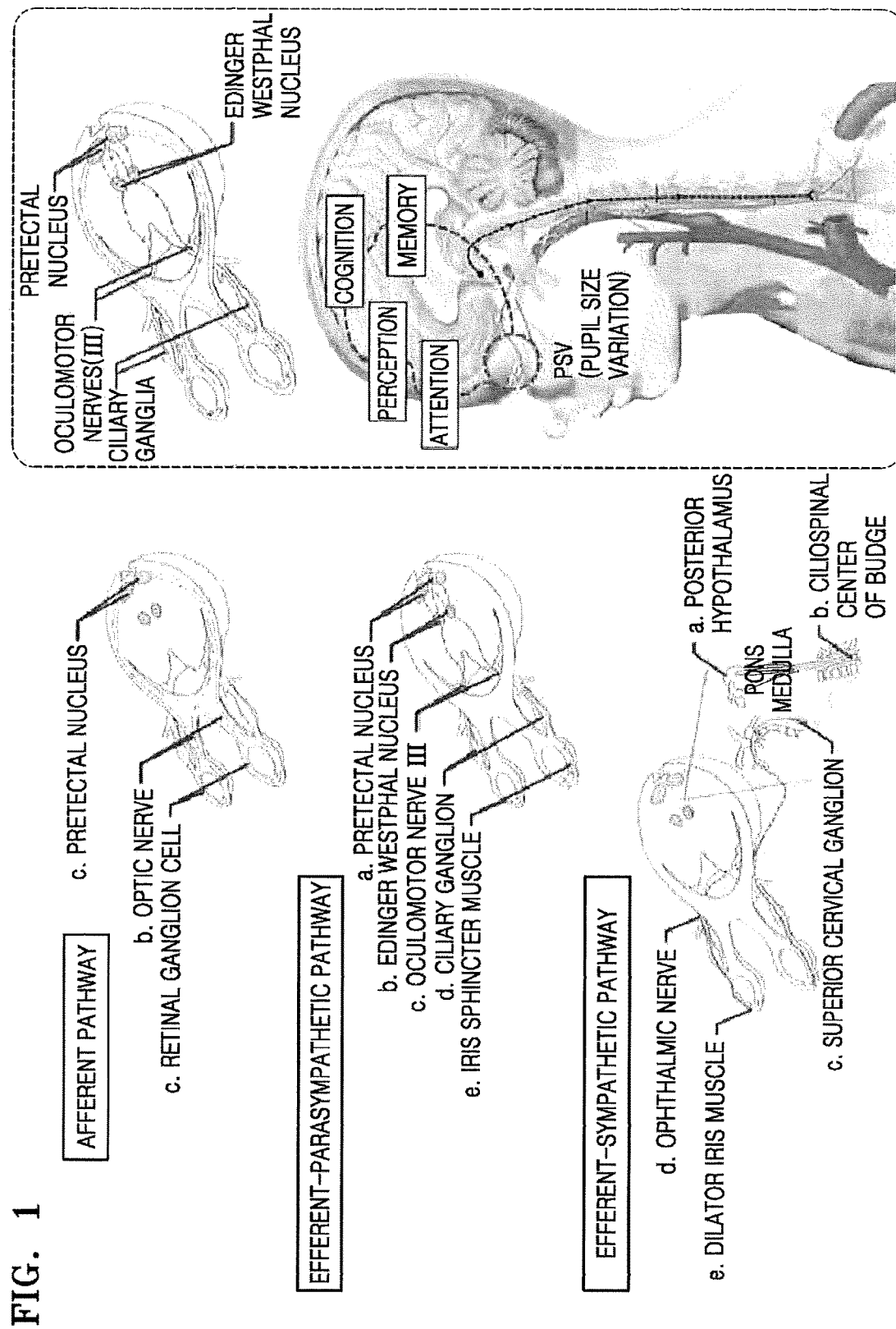
FIG. 1 is an overview of a neural pathway between pupil and brain based on afferent and efferent pathways.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Hereinafter, a method and system for inferencing and detecting physiological signals according to the present inventive concept is described with reference to the accompanying drawings.

The invention may, however, be embodied in many different forms and should not be construed as being limited to the embodiments set forth herein; rather, these embodiments are provided so that this disclosure will be thorough and complete, and will fully convey the concept of the invention to those skilled in the art. Like reference numerals in the drawings denote like elements. In the drawings, elements and regions are schematically illustrated. Accordingly, the concept of the invention is not limited by the relative sizes or distances shown in the attached drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, numbers, steps, operations, elements, and/or components, but do not preclude the presence or addition of one or more other features, numbers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present application, and will not be interpreted in an overly formal sense unless expressly so defined herein.

The embodiments described below involve processing Pupil size variation (PSV) to evaluate noncontact 3D cognitive fatigue from moving images of subjects.

FIG. 1 shows details of the neural network, especially overview of neural pathway between pupil and brain based on afferent and efferent pathway.

The PSV is closely related to central nervous system (CNS) via neural pathway (afferent and efferent). While visualizing the contents, the eyes, specifically the photosensitive retinal ganglion cells from the retina receptors, transmit the visual information to the optic nerve, through the optic disc, and to a synapse in the pretectal nucleus of the upper mid-brain. The pretectal nucleus then transmit the visual information to the Edinger-Westphal nucleus, one of the nuclei of oculomotor. The oculomotor nerve and the ophthalmic nerve are then innervated in addition to the nervous control of the pupil size via the sphincter and dilator muscles, respectively. The PSV also is functionally influenced by cognitive load, perception, memory, attention, and brain activity.

Thus, the 3D visual fatigue shows the relationship with cognitive function such as cognitive load and attention level. Therefore, the PSV, which is affected by the cognitive load, is suggested to be an indicator for the 3D cognitive fatigue. The pupil diameter is increased when increasing process loading (cognitive load) of the human brain. Other studies reported that the higher cognitive load increases the pupil diameter, mean pupil diameter change (MPDC), task-evoked pupillary response (TEPR) amplitude and duration. The ratio between low (LF, 0-1.6 Hz) and high frequency (HF, 1.6-4 Hz) of pupil diameter is a significantly lower under cognitive load. Therefore, the pupil rhythm is related to the cognitive load and observed to be a measurement of 3D cognitive fatigue.

The study for the present invention evaluated a method for measuring 3D cognitive fatigue based on the pupillary response overcoming measurement burden by using noncontact methods. The 3D cognitive fatigue is assessed by TEPR latency of pupillary response. The study also observed other indicators for 3D cognitive fatigue: subjective rating (visual stress, eye pain, body pain, and image blurring), performance (accuracy, response time), ERP (latency), and HEP (alpha activation). The result of TEPR latency was then compared with other indicators using by the Multitrait-Multimethod (MTMM) matrix (test-retest reliability, discriminant, and convergent validity).

The evaluation method according to the exemplary embodiments is based on image data acquired in noncontact, thus reduce or remove measurement burden by attachment of sensors.

The system adopting the method of cognitive fatigue is based on a computer-architecture along with infrared camera.

That is, the system according to the exemplary embodiment comprises:

an infrared movie camera, such as a webcam, taking face images of subjects;

an image processing unit for treating or processing the images from the infrared movie camera; and an analysis unit for calculating TEPR from the PSV extracted from the face images, extracting latency of the dominant peak of the TEPR and determine cognitive fatigue by comparing the latency with a reference.

Here, the image processing unit, analysis unit, and the like may be implemented by a hardware-based software apparatus of a computer system.

Figure 2:
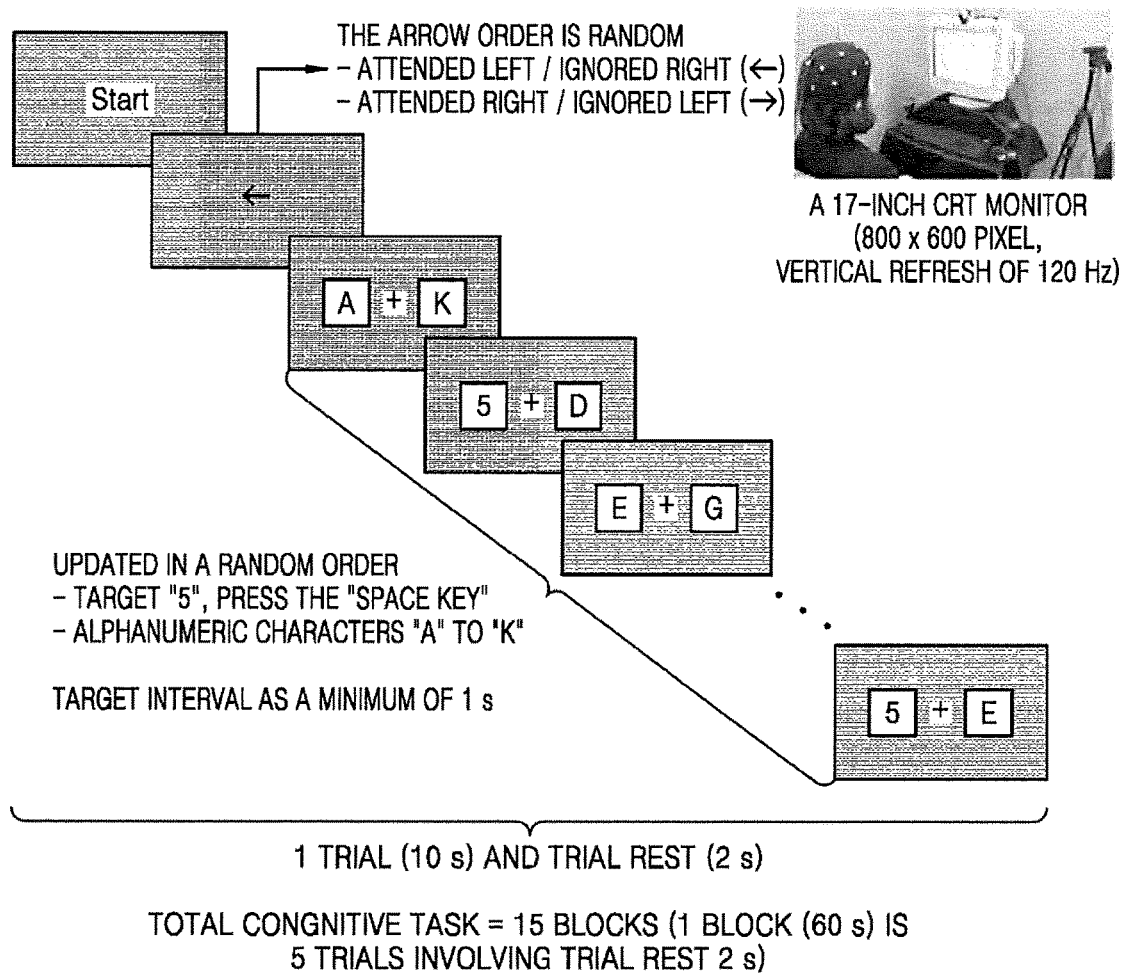
FIG. 2 shows an experimental procedure in relation to cognitive load according to an experiment of an exemplary embodiment.
Figure 3:
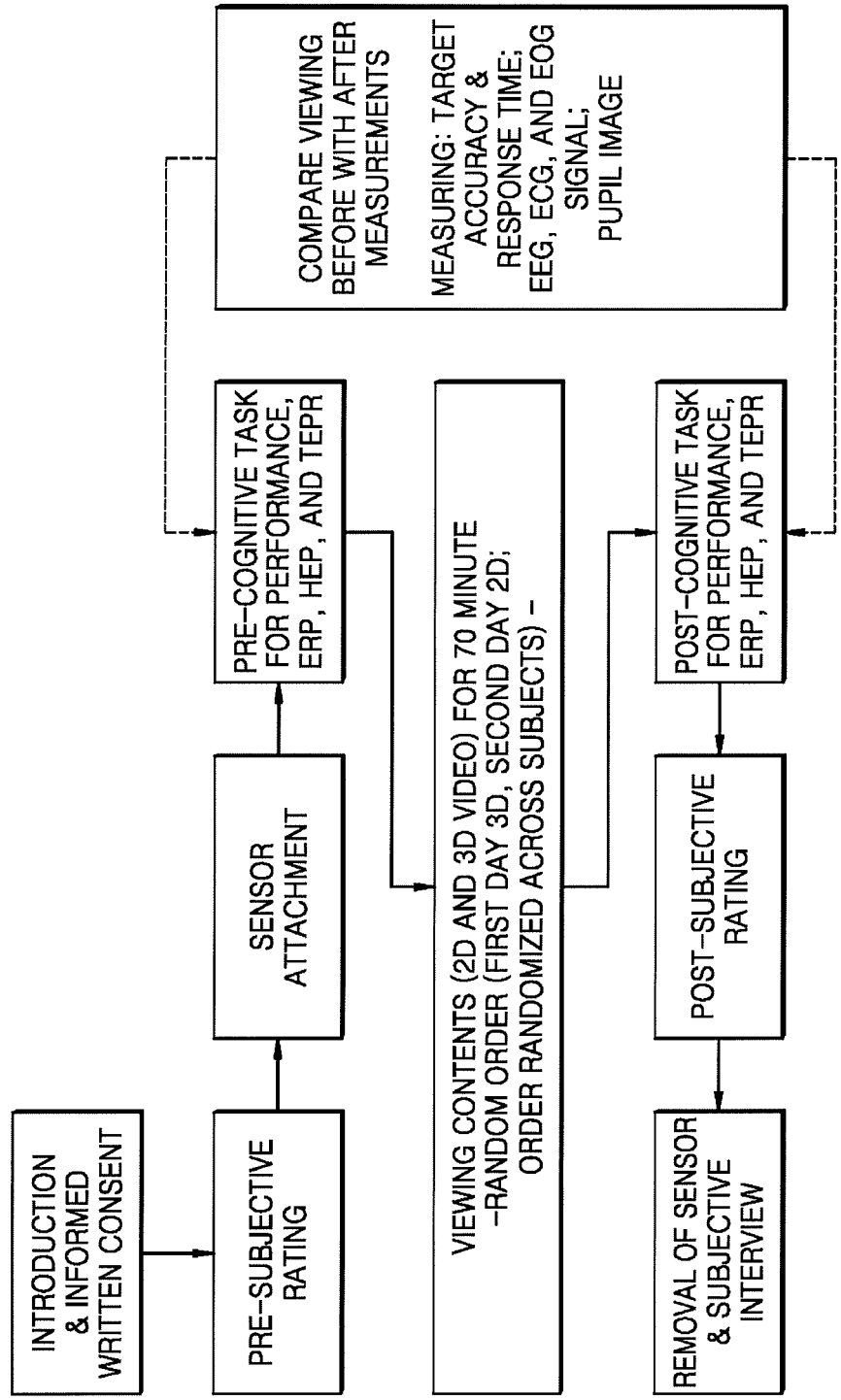
FIG. 3 shows the flow of the procedure of the experiment according to an exemplary embodiment.
Figure 4:
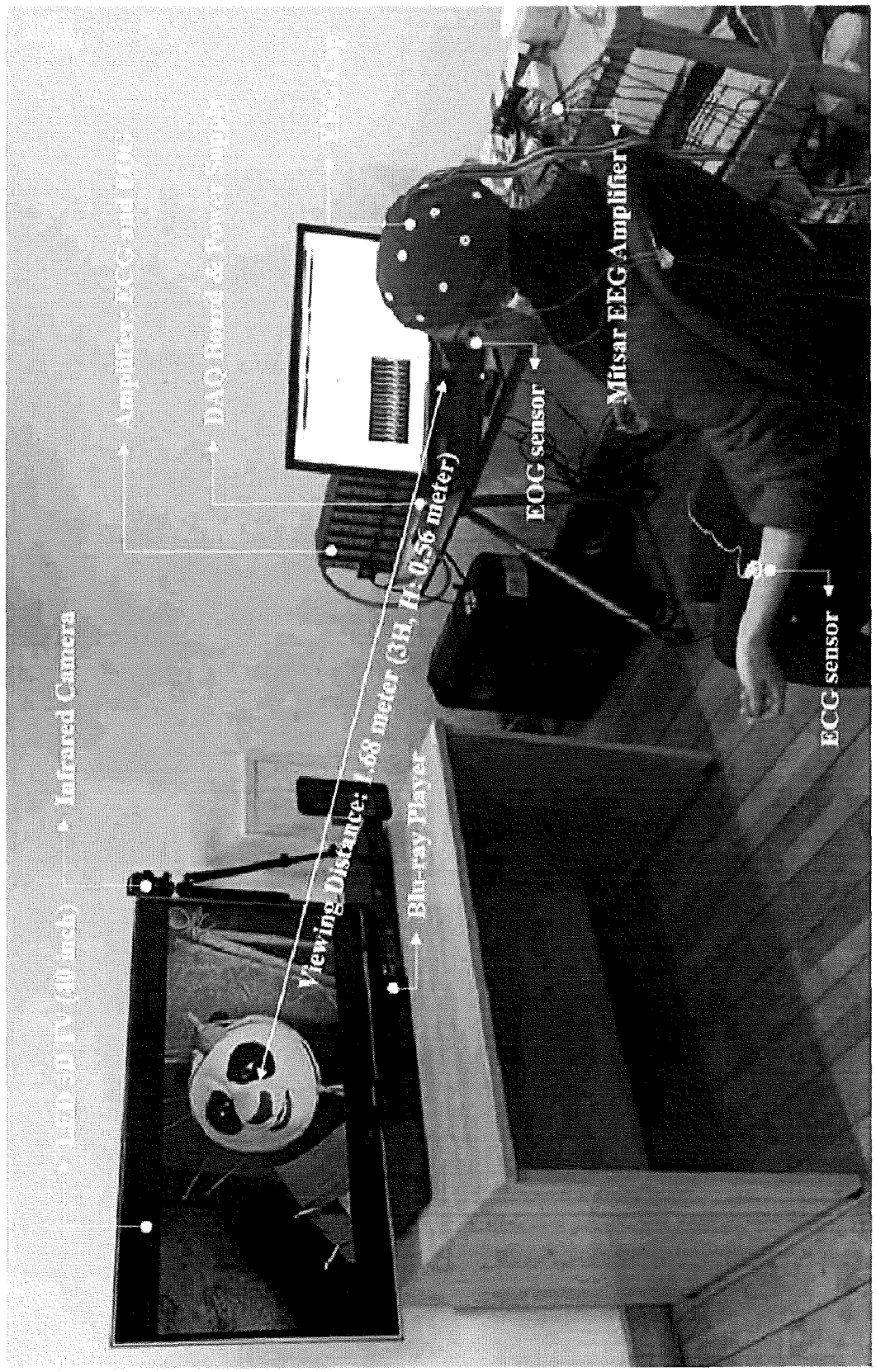
FIG. 4 shows an actual experimental apparatus and environment, according to an exemplary embodiment.

FIG. 2 shows an experimental stimulus and its procedure for the load of cognitive fatigue according to the experiment of the present invention. FIG. 3 schematically shows the flow of the procedure of the experiment according to the invention. FIG. 4 shows an actual experimental apparatus and environment according to the present invention.

Participant

Thirteen undergraduate students (7 females), ranging in age from 23 to 31 years old (mean 26.5±0.1) participated in the experiment. All participants had right-handed, and normal or corrected to normal vision (i.e., over 0.8). They had no family or medical history of cardiovascular, central nervous, and vision disease. Every participant was individually informed to abstain from the alcohol, cigarettes, and caffeine for 24 hours prior to the experiment, and to get a full night's sleep. Also, the consents, defining the participants were notified with restrictions and requirements, were received. All protocols used in this experiment were approved by the Institutional Review Board of Sangmyung University, Seoul, South Korea.

Stimuli for ERP, HEP, and TEPR

A stimulator, to measure ERP and TEPR response (cognitive load), was developed utilizing previous studies (Mun et al., 2012; Park et al., 2014; Park et al., 2015). The stimulator randomly produced 12 alphanumeric characters (non-target: "A"–"K"+target: "5"). The alphanumeric characters were updated at a rate of 6 Hz. One trial consisted of 5 sequences involving 60 alphanumeric characters with a length of 10 seconds. One block consisted of 5 trials (60 seconds) involving the trial interval of 2 seconds. Total task had 15 blocks. The interval between targets, the randomly generated alphanumeric characters, was set to a minimum of 1 second to avoid over lapping ERP and TEPR data (data separation problems). To participants, the stimuli were presented on the left and right sides of the screen. The cross hair was located in the center of screen. Then, the direction, where to put attention or ignore (attended target), was notified to participants with an arrow.

Experimental Procedure

FIG. 3 illustrates the overall experimental procedure according to an embodiment. Each participant was required to report visual state using subjective rating. Subjective rating was composed of 4 factors such as visual stress (VS, 15 items), eye pain (EP, 10 items), body pain (BP, 4 items), and image blurring factor (IBF, 4 items) (Li, 2010). The participant was also asked to self-report subjective visual discomfort using 1 to 5 points scale for 33 items in both before and after viewing the video. Each subject, before the cognitive task, conducted a training task to minimize the learning effects and maximize the performance. The training session was conducted until each subject accomplishes a high accuracy, higher than 80%, of defining the target. To minimize the visual fatigue, the participants were assigned with 10-minute break, and then continued with the cognitive task. During cognitive task, they were required to detect a target of attended direction by hitting the space bar on a keyboard as soon as possible. The monitor used in this experiment was a 17-inch LCD monitor having a resolution of 800×600 and a vertical refresh rate of 120 Hz. The distance from the participant's eyes to the stimulator display was approximately 60 centimeters. During the task, the participants were asked to fix their eyes on a pair of crosshairs and to focus on the attended target. The performance was defined with the accuracy of target response and the response time with the reaction lag of target response. The reaction times between 200 and 1200 milliseconds after target onset were considered as valid responses for further analysis. The EEG, electrocardiogram (ECG), pupillary variation data, and the response time during target presentation were utilized as an input to the ERP, HEP, and TEPR analysis. These analyses also were conducted both before and after viewing a video content.

The participants viewed "Kung Fu Panda 3" (DreamWorks Animation Oriental DreamWorks, 20th Century Fox CJ Entertainment, 2016)—in both 2D and 3D versions over the course of the experiment. In this experiment, the participant viewed either the 2D or 3D version of the video contents (randomized) on first experiment day and the other dimensionality on the next experiment day (e.g., first day 3D, second day 2D; orders were randomized for all subjects). A blu-ray player (BD-ES6000, Samsung) was used to play the 2D and 3D contents on an LED-3DTV (UN40ES6800F, Samsung) with the following specifications:

3D type: Active Shutter Glass
Size: 40 inches (width: 936 mm, height: 559 mm).
Spatial resolution: 1920 pixels×1080 pixels.
Aspect ratio: 16 (horizontal):9 (Vertical)
Ratio of brightness to darkness: over 1,000,000:1 (mega DCR).

The participants viewed the video, both 2D and 3D, contents for 70 minute in home-like environment. The viewing distance was 1.68 meter from screen. The distance was calculated using the 3DC Safety Guidelines where distance should equal to 3 times of the height of the screen. FIG. 4 shows an example of experiment environment for this experiment.

Data Acquisition and Signal Processing

Figure 15:
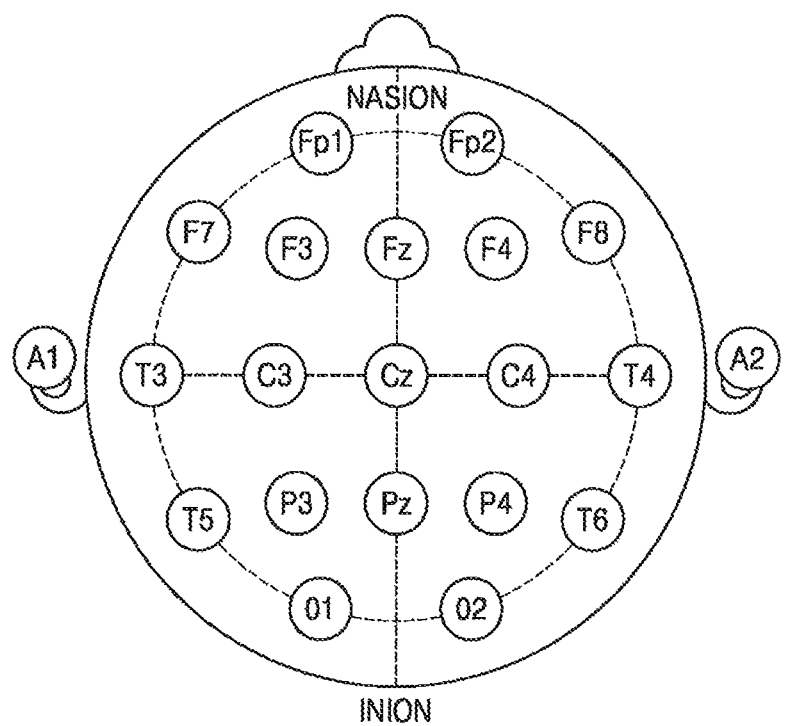
FIG. 15 shows an arrangement of electroencephalogram (EEG) electrodes of international 10-20 system.

EEG, electrooculogram (EOG), ECG, and pupil images were measured both before and after each viewing. EEG signals were recorded at a 500 Hz sampling rate from eight channels on the scalp at positions F3, F4, C3, C4, P3, P4, O1, and O2 based on the international "10-20" system (ground: FAz, reference: average between electrodes on the two ears, and DC level: 0 Hz-150 Hz) as shown in FIG. 15, and using a Mitsar-EEG 202 Machine (Mitsar Inc., Russia). The electrode impedance was kept below 3 kΩ. ECG and EOG signals were recorded at a 500 Hz sampling rate using an amplifier system (ECG 100C and EOG 100C amplifiers in BIOPAC system Inc., USA), digitized with the DAQ- Board (NI-DAQ-Pad9205 in National Instrument Inc., USA), and MP100 power supply (BIOPAC system Inc., USA).

ECG signals were measured from one channel using Lead-III method. EOG signals were measured from two channels, the vertical and the horizontal, to permit removal of the blinking artifact. Pupil images were recorded at 125 fps with a resolution of 960×400 by using a GS3-U3-23S6M-C infrared camera (Point Grey Research Inc., Canada).

Figure 5:
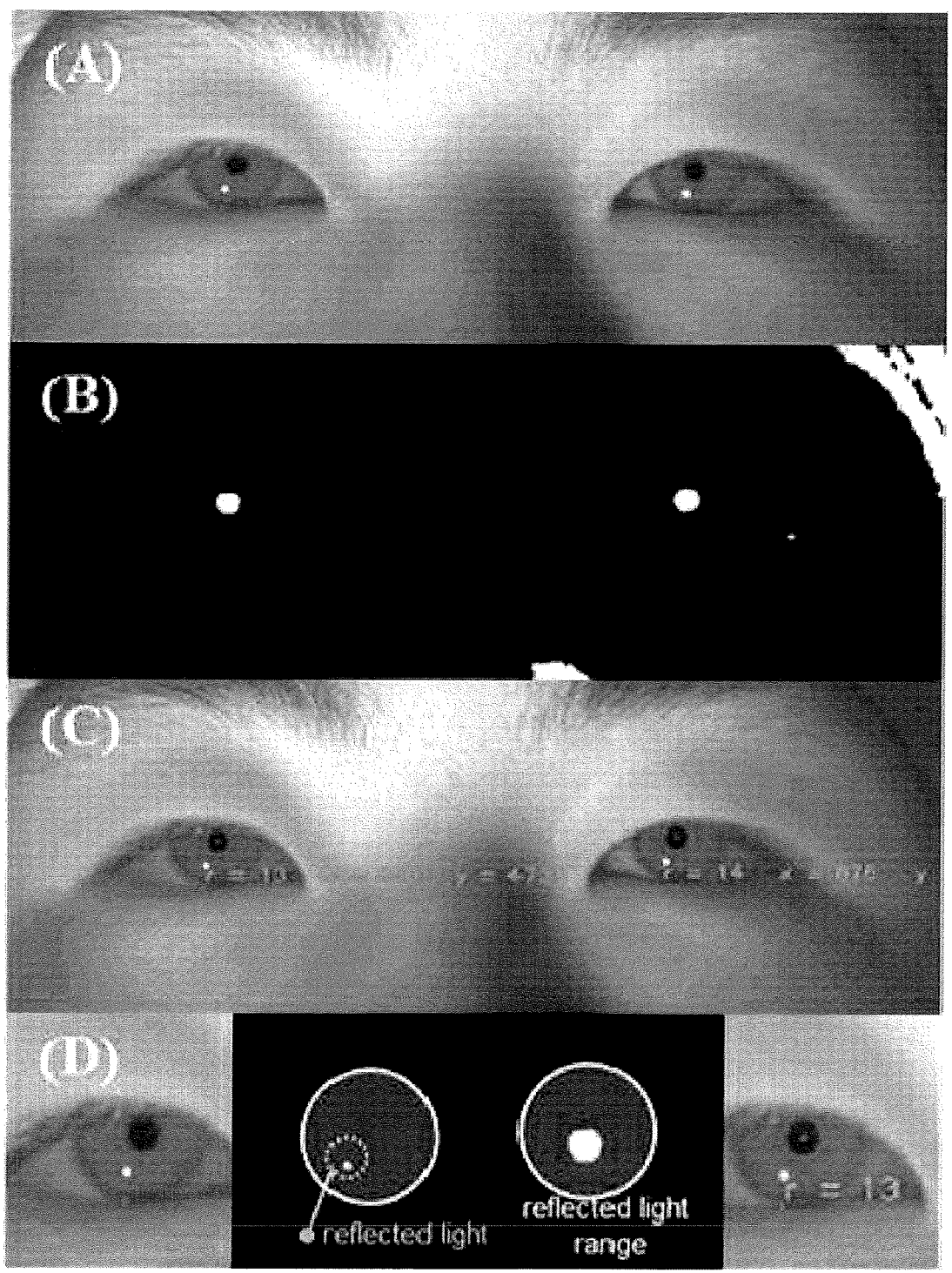
FIG. 5 shows steps for detecting pupil regions from a captured image, according to an exemplary embodiment.

As shown in FIG. 5, the images, from the pupil detection, captured with infrared camera needed an image processing. A gray scale image from infrared camera was first binarized with the specific threshold value, which was determined by using the method proposed by Gonzalez and Woods (2002). The pupil region was detected by Circular Edge Detection (CED) algorithm with the basis of the following Equation 1 (Daugman, 2004; Lee et al., 2009; Lee et al., 2010):

$$\max_{(r,x_0,y_0)} \left| G_\sigma(r) \cdot \frac{\partial}{\partial r} \oint_{r,x_0,y_0} \frac{I(x,y)}{2\pi r} ds \right| \quad \langle \text{Equation 1} \rangle$$

where $I(x,y)$, $(x_0, y_0)$, and $r$ are the $(x,y)$ positions in a gray scale of detected center location, and radius of a pupil.

Figure 6:
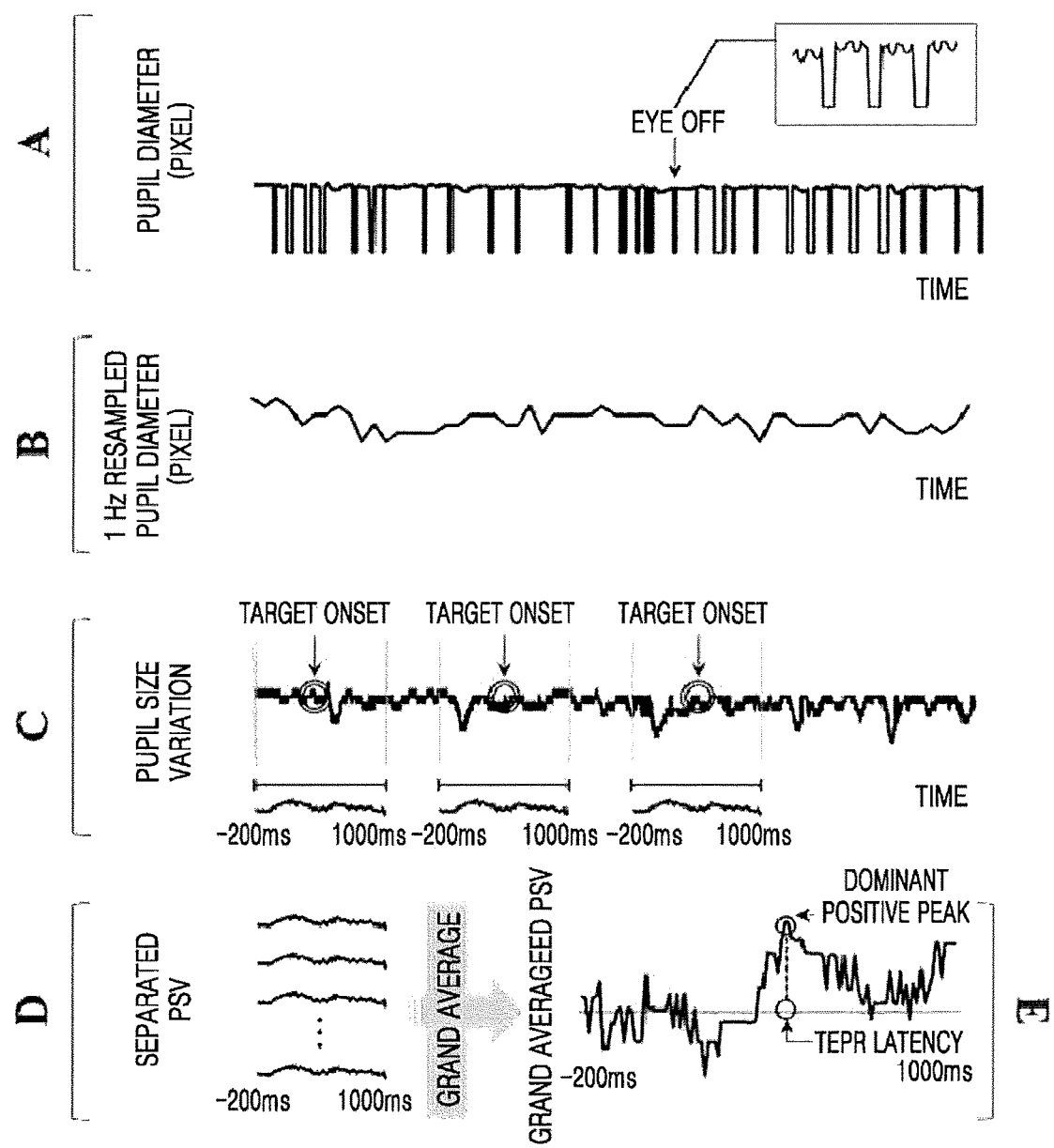
FIG. 6 shows signal processing progress for task-evoked pupillary response (TEPR) latency and definition thereof, according to an exemplary embodiment.

FIG. 6 shows signal processing for TEPR latency and definition thereof.

(1) The pupil diameter was calculated or extracted from detected pupil area.

(2) The calculated or extracted pupil diameter is resampled (window size: 1 s, resolution: 1 s) to 1 Hz, except for the non-detected pupil interval due to eye blinking.

(3) Pupil diameter resampled to 1 Hz is calculated or extracted as PSV data through the difference value between the previous pupil diameter data, respectively.

(4) The Pupil Size Variation (PSV), i.e., the pupil size signal, is divided into epochs of 1200 ms based on Target (Stimulus) Onset (−200 to 1000 milliseconds). The data divided by the predetermined fixed time interval is unit PSV.

(5) The divided unit PSVs based on the target stimulus is combined by using the grand average technique to calculate or produce the TEPR.

(6) Latency is obtained or calculated from the TEPR. The TEPR latency is defined as the time value of the dominant positive peak. This dominant positive peak was assigned as the indicator of cognitive fatigue in this experiment as shown FIG. 6.

Figure 7:
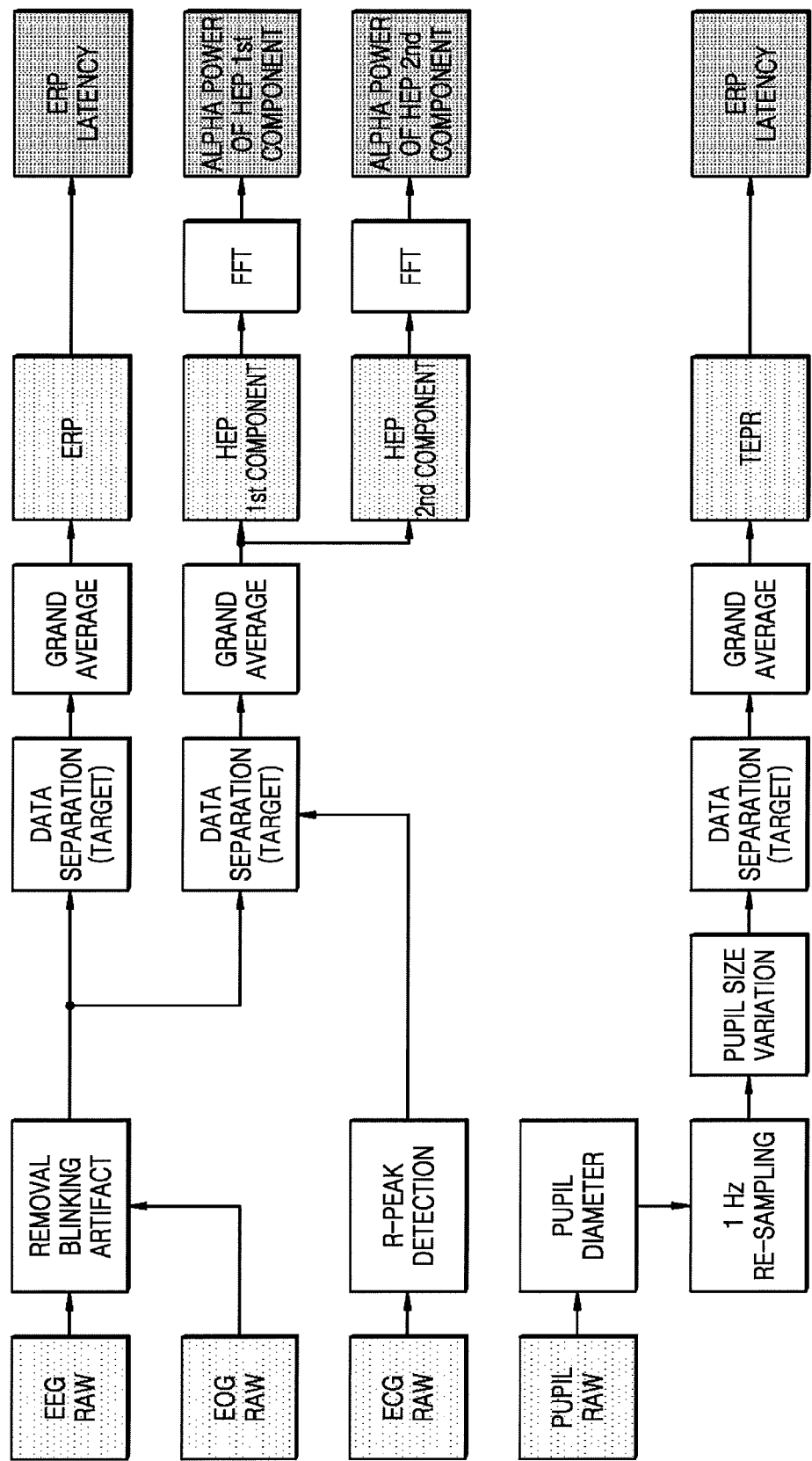
FIG. 7 is a block diagram showing signal processing for analysis of event-related potential (ERP), heartbeat evoked potential (HEP), and TEPR, according to an exemplary embodiment.

In addition, the ERP latency (Mun et al., 2012; Park et al., 2015) and alpha power of HEP (Park et al., 2015) were extracted using the same method utilized in the previous study. FIG. 7 shows signal processing progress for analysis of ERP, HEP and TEPR.

Statistical Analysis

This experiment was designed to test and compare the viewer's experience for 3D cognitive fatigue while experiencing both 2D and 3D contents "within subject design." Mann-Whiteny test was tested with normality test.

The Bonferroni correction was performed to derive statistical significances while to resolve the problem caused by multiple comparison. All measurements were calculated by subtracting the value measured before and after viewing. The statistical significant level was controlled based on the number of each individual hypothesis (i.e., $\alpha = 0.05/n$).

For this experiment, the statistical significant level of each measure was set up 0.0125 (subjective evaluation, $\alpha = 0.05/4$) and 0.0019 (performance, ERP, and HEP, $\alpha = 0.05/26$), respectively. Also, in order to confirm practical significance, the effect-size based on absolute value of r (non-parametric) was also calculated. In this case, the r's standard values were 0.10, 0.30, and 0.50, which, for effect-size, were generally regarded as small, medium, and large.

In addition, to verify test—retest reliability, convergent validity, and discriminant validity among various 3D cognitive fatigue indicators-such as subjective evaluation, performance, ERP, HEP, and TEPR-MTMM (multi-trait and multi-method) matrix was used. If the attributes of data sample were determined to be multi-trait and multi-method, the MTMM matrix confirmed the relationship between multiple measures.

By confirming the monomethod—monotrait (reliability diagonal), monomethod—heterotrait, and heteromethod—monotrait, the test—retest reliability, discriminant validity, and convergent validity were tested and verified.

Subjective Evaluation

Figure 8:
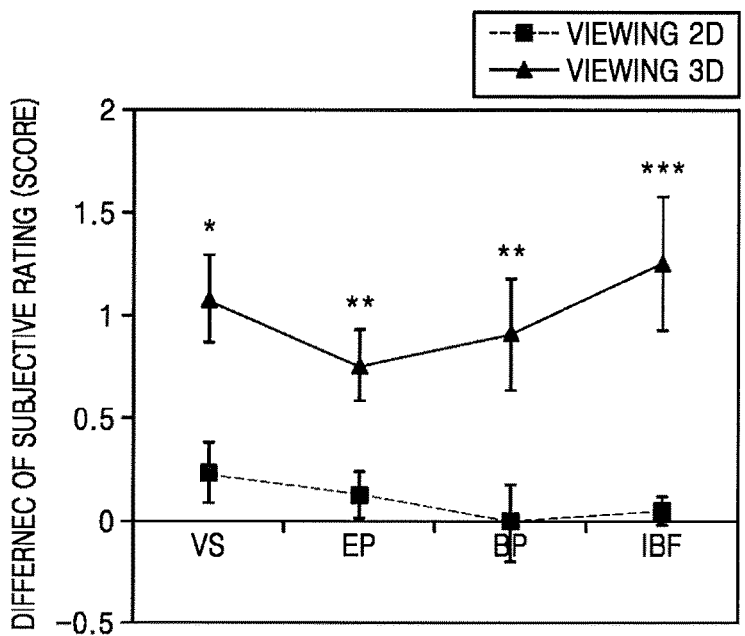
FIG. 8 shows differences between average subjective ratings of four factors for 2D and 3D conditions, according to an exemplary embodiment.

FIG. 8 shows differences of average subjective rating of four factors for 2D and 3D conditions. The subjective scale was evaluated with a five-point scale about each four components (VS: Visual Stress; EP: Eye Pain; BP: Body Pain; IBF: Image Blurring Factor), and it was calculated with the difference value between before and after each viewing condition (*, $p<0.05$; , $p<0.0125$; *, $p<0.001$).

As shown in FIG. 8, the subjective ratings in the 3D viewing conditions were significantly increased compared to the 2D viewing conditions for Eye Pain ($Z=-2.729$, $p=0.0064$, $r=0.535$ with large effect size), Body Pain ($Z=-3.044$, $p=0.0023$, $r=0.597$ with large effect size), and Image Blurring Factor ($Z=-2.878$, $p=0.0001$, $r=0.761$ with large effect size).

The mean (M) and standard deviation (SD) of significant difference of the subjective ratings were found as following: EP (2D: M=0.131, SD=0.434, 3D: M=0.631, SD=0.670), BP (2D: M=−0.012, SD=0.729, 3D: M=0.923, SD=1.044), and IBF (2D: M=0.051, SD=0.257, 3D: M=1.208, SD=1.271). Although the VS items of 3D viewing condition were accumulative compared to the 2D viewing condition, it did not show significance ($Z=-2.311$, $p=0.0208$, $r=0.453$ with large effect size).

Performance

Figure 9:
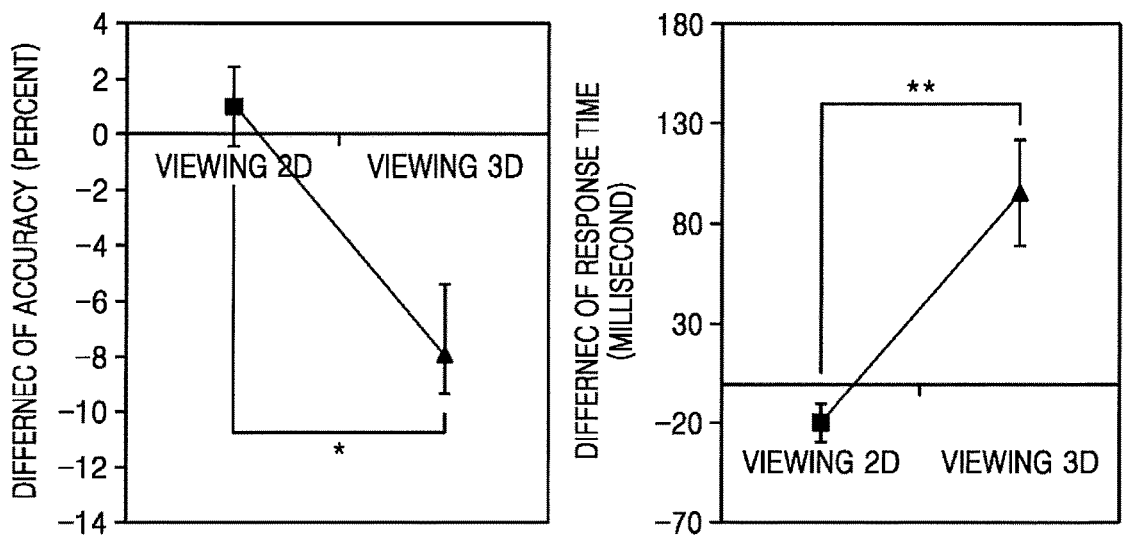
FIG. 9 shows average accuracy and response time for presented target for 2D and 3D conditions according to an exemplary embodiment.

FIG. 9 shows average accuracy (left) and response time (right) for presented target for 2D and 3D conditions. Both values was calculated with the difference value between before and after each viewing condition (*, $p<0.05$; **, $p<0.0019$).

The performances this experiment focused were the accuracy and response time for the targets. As shown in FIG. 9, the accuracy of 3D viewing conditions was decreased comparing to the 2D viewing conditions. However, the decrease was not significant ($Z=-2.489$, $p=0.0128$, $r=0.488$ with large effect size). The mean (M) and standard deviation (SD) values for the difference of the performance resulted as following values: response time (2D: M=−19.854, SD=35.949, 3D: M=95.256, SD=102.833). The response time in the 3D viewing condition was significantly decreased comparing to the 2D viewing condition ($Z=-3.154$, $p=0.0016$, $r=0.619$ with large effect size).

ERP Latency

Figure 10:
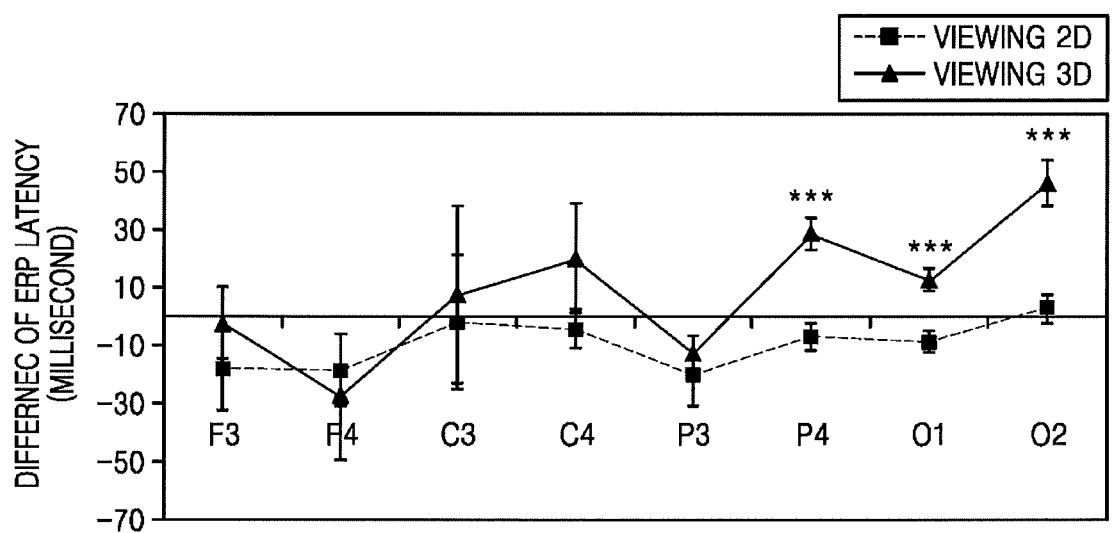
FIG. 10 shows averages of ERP latency in eight brain regions for 2D and 3D conditions according to an exemplary embodiment.

FIG. 10 shows averages of ERP latency in eight brain regions for 2D and 3D conditions. The ERP latency values (P600) were calculated with the difference value between before and after each viewing condition (***, p<0.001).

As shown in FIG. 10, the ERP latency in the 3D viewing condition showed delay comparing to the 2D viewing condition in the regions of P4 (Z=−3.853, p=0.0001, r=0.756 with large effect size), O1 (Z=−3.772, p=0.0002, r=0.740 with large effect size), and O2 (Z=−3.928, p=0.0001, r=0.770 with large effect size). No significant effects were found for the other brain regions (F3, F4, C3, C4, and P3). The significant difference of the ERP latency increases was detected in P600 at P4 (2D: M=−7.077, SD=17.429, 3D: M=35.538, SD=21.925), O1 (2D: M=−8.769, SD=14.434, 3D: M=21.692, SD=14.290), and O2 (2D: M=−2.615, SD=19.931, 3D: M=43.385, SD=31.057).

Alpha Power of HEP

Figure 11:
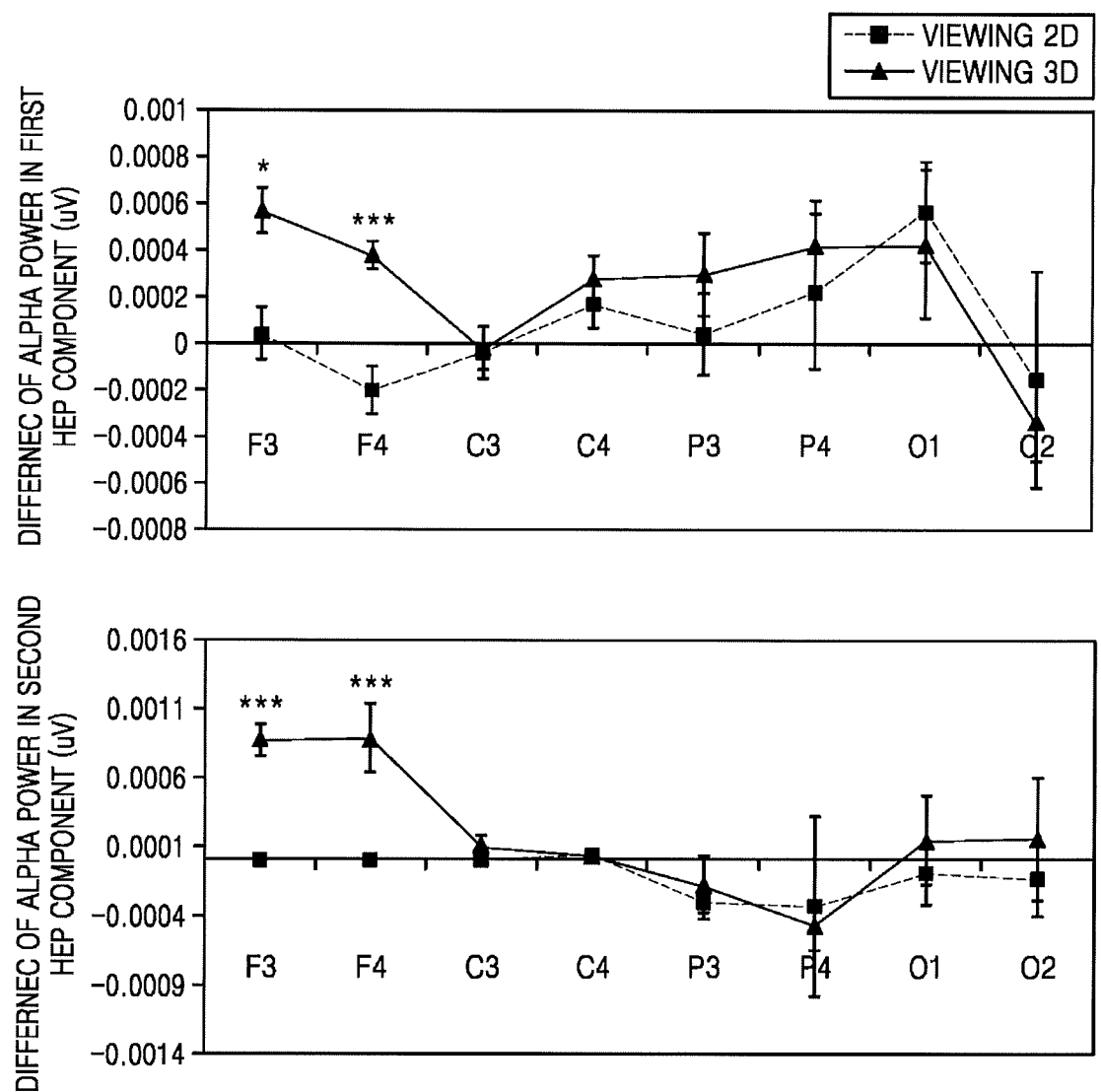
FIG. 11 shows average values for the HEP first and second components in eight brain regions for 2D and 3D conditions, according to an exemplary embodiment.

FIG. 11 shows average values for the HEP first (alpha power in 50-250 ms period after the R-peak) and second (alpha power in 250-600 ms period after the R-peak) components in eight brain regions for 2D and 3D conditions. This values were calculated with the difference value between before and after each viewing condition (*, p<0.05; , p<0.0019; *, p<0.001)

As shown in FIG. 11, the alpha power of the first HEP component showed significant increase in the 3D viewing condition compared to the 2D viewing condition in the regions of F4 (Z=−3.359, p=0.0008, r=0.659 with large effect size).

The mean (M) and standard deviation (SD) for the difference of alpha power in first HEP component resulted as following: F4 region (2D: M=−0.00020, SD=0.00039, 3D: M=0.00058, SD=0.00022). The significant result was not found in other brain regions (F3, C3, C4, P3, P4, O1, and O2).

The alpha power of the second HEP component also showed significant increase in the 3D viewing condition compared to the 2D viewing condition in the regions of F3 (Z=−4.282, p=0.0001, r=0.840 with large effect size) and F4 (Z=−4.231, p=0.0001, r=0.830 with large effect size).

The mean (M) and standard deviation (SD) for the difference in the alpha power of second HEP component resulted as following: F3 region (2D: M=−0.00001, SD=0.00017, 3D: M=0.00088, SD=0.00044) and F4 region (2D: M=−0.00001, SD=0.00089, 3D: M=0.00089, SD=0.00095). The significant result was not founded in other brain regions (C3, C4, P3, P4, O1, and O2).

TEPR Latency

Figure 12:
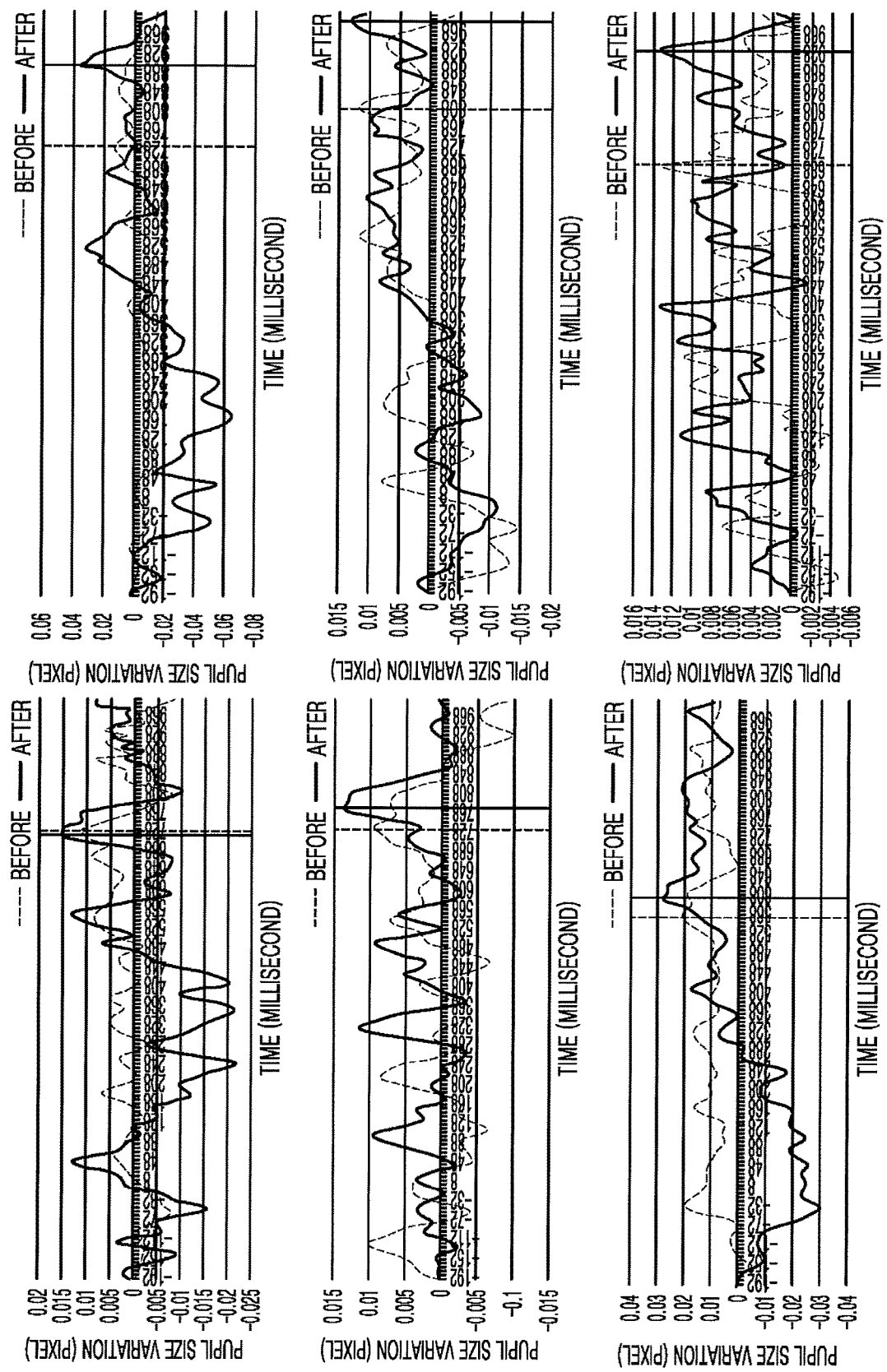
FIG. 12 shows examples of change in TEPR latency before and after viewing 2D and 3D contents, according to an exemplary embodiment.

FIG. 12 shows examples of change in TEPR latency before and after viewing 2D and 3D contents for participants 3, 7, and 12. In FIG. 12, three graphs on the left are for 2D content and there graphs on the right is for 3D content. The TEPR latency is shown by a dotted line for viewing before and a solid line for viewing after. Difference values of TEPR latency between before and after 2D viewing for participants 3, 7, and 12 were 8 ms, 40 ms, and 40 ms, respectively. Difference values of TEPR latency between before and after 3D viewing for participants 3, 7, and 12 were 168 ms, 176 ms, and 240 ms, respectively.

In the difference of two conditions, the before and after viewing the 2D content, dominant positive peaks in TEPR waveform showed a minute difference there between. As for the 3D content, interestingly, the dominant peak of the after viewing was delayed far away than that of the before viewing.

Figure 13:
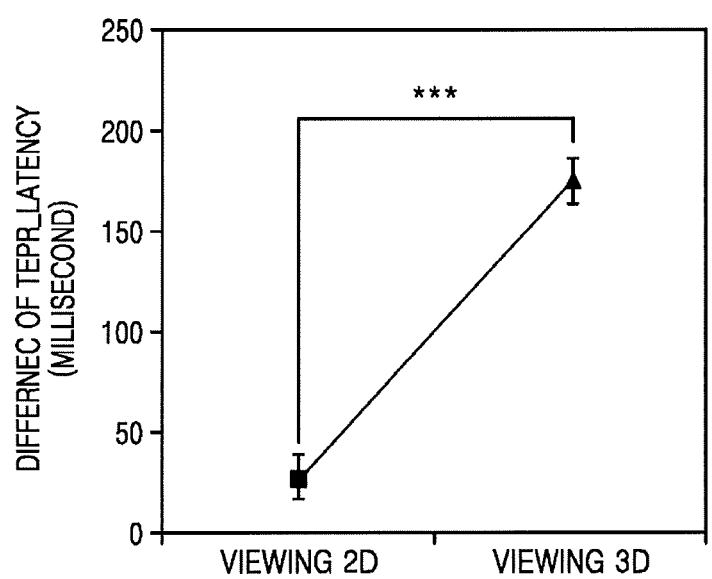
FIG. 13 shows average values of TEPR latency in a pupillary response for 2D and 3D conditions, according to an exemplary embodiment.

FIG. 13 shows average values of TEPR latency in pupillary response for 2D and 3D conditions. The TEPR latency values was calculated with difference values between before and after each viewing condition (***, p<0.001).

As shown in FIG. 13, the value of TEPR latency in the 3D viewing condition was higher than that in the 2D viewing condition (Z=−4.185, p=0.0001, r=0.821 with large effect size). The mean (M) and standard deviation (SD) for the difference of the TEPR latency resulted as following: TEPR latency value (2D: M=27.077, SD=46.281, 3D: M=176.000, SD=38.431)

MTMM Matrix

A test re-test reliability, discriminant validity, and convergent validity between the measurements of visual fatigue were compared by utilizing the Multitrait-multimethod (MTMM) analysis. This experimental design defined that multi-method was included in 2D and 3D viewing conditions. Also, the multi-trait was involved in measurements of the visual fatigue such as the subjective rating factors (EP, BP, and IBF), Performance factor (response time), ERP latency factors (latency of brain regions at P4, O1, and O2), HEP factors (alpha activity of HEP first component of brain region at F4, and second component of brain regions at F3 and F4), and TEPR factor (TEPR latency) based on corrected statistical significance measures, as shown in table of FIG. 14.

Figure 14:
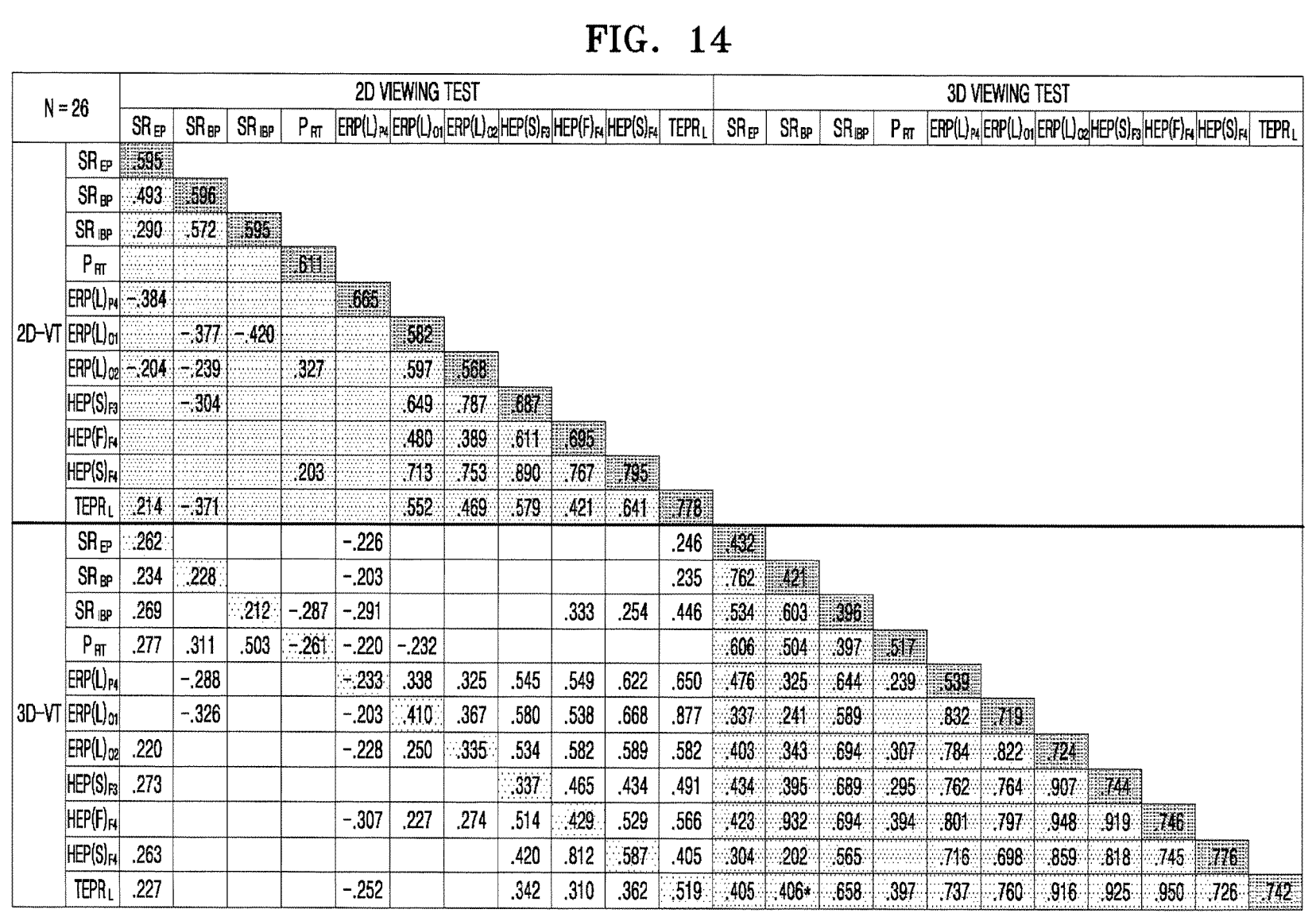

FIG. 14 shows a Multitrait-multimethod (MTMM) matrix of the correlation coefficients between subjective evaluation, performance, and ERP latency, alpha power of HEP, and TEPR latency with 2D and 3D viewing tests.

In the table of FIG. 14, the reliability (Cronbach's alpha coefficient) is shown as a main diagonal with black (MTMM). Discriminant validity is shown as a heterotrait-monomethod triangle with light grey. Convergent validity is shown as a monotrait-heteromethod diagonal with dark grey. Correlation coefficients between other traits are not shown when smaller than 0.20 (p>0.01). The abbreviation in the table followed that; $SE_{EP}$, $SE_{BP}$, and $SE_{IBF}$-subjective ratings (eye pain, body pain, and image blurring factor); $P_{RT}$-performance (reaction time); $E(L)_{P4}$, $E(L)_{O1}$, and $E(L)_{O2}$-ERP latency (P4, O1, and O2 brain regions); $H(F)_{F4}$-HEP first component (F4 brain region); $H(S)_{F3}$ and $H(S)_{F4}$-HEP second component (F3 and F4 brain regions); T(L)-TEPR latency.

The validity of the test re-test was defined with the main diagonal of MTMM matrix between the 2D and 3D viewing conditions (multi-method).

As shown in FIG. 14, the subjective rating, $SR_{EP}$, $SR_{BP}$, and $SR_{IBF}$ showed low reliability in both 2D (0.595, 0.596, and 0.595) and 3D (0.432, 0.421, and 0.396) viewing test. The performance ($P_{RT}$) also shows low reliability in both 2D (0.611) and 3D (0.517) viewing test. The ERP latency at the P4 region ($ERP(L)_{P4}$) shows low reliability in both 2D (0.665) and 3D (0.539) viewing test. The ERP latency at the O1 and O2 regions ($ERP(L)_{O1}$ and $ERP(L)_{O2}$) showed low reliability in the 2D viewing test (0.582 and 0.568), but showed high reliability in the 3D (0.719 and 0.714). The HEP alpha power in the first component at the F4 region ($HEP(F)_{F4}$) showed low reliability in the 2D viewing test (0.695), but showed high reliability in the 3D (0.746). The HEP alpha power in the second component at F3 region (HEP(S)$_{F3}$) showed low reliability in the 2D viewing test (0.687), but high reliability in the 3D (0.744). The HEP alpha power in the second component at F4 region (HEP (S)$_{F4}$) showed high reliability in both 2D (0.795) and 3D (0.776) viewing test.

The TEPR latency (TEPR$_L$) showed high reliability in both 2D (0.778) and 3D (0.742) viewing test. The reliability coefficients between the 2D and 3D viewing tests were internally consistent with the HEP alpha power in second component at F4 region and TEPR latency rather than other measures. The validity of discriminant validity was determined with the heterotrait-monomethod triangles. The TEPR latency resulted in the high correlation coefficients with ERP (0.469 to 0.916) and HEP measures (0.421 to 0.966). The correlation coefficients between TEPR latency and HEP second component (F4 regions) showed a strong positive correlation (0.641 to 0.966). However, the correlation coefficients between TEPR latency and other measures were relatively low (−0.371 to 0.458) compared to HEP and ERP measures. The correlation coefficients between the HEP/ERP and other measures have also been relatively low (−0.371 to 0.694/−0.420 to 0.694). The discriminant validity was not robust between the ERP, HEP, and TEPR measures. These measures had a difference with subjective ratings and performance measures.

The validity of convergent was defined with the monotrait-heteromethod diagonal. The subjective rating such as SR$_{EP}$, SR$_{BP}$, and SR$_{IBF}$ showed low correlation at 0.212 to 0.262. The performance (P$_{RT}$) showed low correlation at −0.261. The ERP latency at P4, O1, and O2 regions (ERP (L)$_{p4}$, ERP(L)$_{O1}$, and ERP(L)$_{O2}$) showed low correlation at −0.233 to 0.335. The HEP measures (HEP(F)$_{F4}$, HEP(S)$_{F3}$, and HEP(S)$_{F4}$) showed medium correlation at 0.337 to 0.587. The TEPR latency (TEPR$_L$) showed medium correlation at 0.519. The HEP (HEP(S)$_{F4}$) and TEPR latency (TEPR$_L$) measure had higher correlation (0.587 and 0.519) rather than other measures

DISCUSSION

The 3D visual fatigue has been researched for the method to measure and quantify in order to improve viewer experience. The visual fatigue was found to be the result of the degradation of cognitive processing rather than the visual discomfort. The ERP and HEP measures related to the cognitive function were proposed by previous researches as the indicator of visual fatigue and showed higher reliability than other indicators. However, these previous indicators for visual fatigue, usually the bio-sensor, were limited in practical applications since sensors were needed to be attached to the skin. To this end, the present invention proposes a new method based on the pupillary response (TEPR latency) overcoming measurement burden by using non-contact methods. The reliability of the method according to an exemplary embodiment of the present invention was approved by comparing with the other measures (subjective rating, performance, ERP, and HEP) by using the MTMM analysis.

The subject rating showed participants experienced the subjective visual fatigue (eye pain, body pain, and image blurring factor) after watching a 3D video, but not after watching the 2D video. The visual fatigue was confirmed to cause by this experiment design based on result of subjective rating. The response time for the target was significantly increased after watching a 3D video than 2D video. Increasing the response time for the target in participants was caused by the viewer experiencing difficulty in focusing their attention on the task, and strongly correlated to increase cognitive load in human brain. In the result, the ERP latency was significantly delayed after participants watched a 3D video comparing to the 2D video. The P300 component of ERP has been well known as the indicator related to the cognitive function. The delaying of the P300 component is correlated to the degradation of the human visual function, that is, cognitive load (fatigue). Previous research reported significant delay in ERP latency from P300 to P600 and P700, and showed the same result in our research.

The alpha power of first and second components in HEP were increased after watching a 3D video than 2D video. The alpha power of first (50-250 ms after the R-peak) and second (250-600 ms after the R-peak) components in HEP showed the time interval required to transmit the cardiac information and the hydraulic blood pressure wave in the heart to travel to the brain through afferent pathways in the vagus nerve. To increase the alpha power of first and second components meant that the brain required to the cardiac information and blood flow during the communication between heart and brain caused by degradation of the information processing in brain. As mentioned earlier, the visual fatigue, that is cognitive load, was caused by the present experimental design following the result of subjective rating, response time, ERP latencies, and alpha power in HEP first and second components.

In this research, the TEPR latency, similar with the ERP latency, was defined as the time value of the dominant pupillary response from evoked potential in grand averaged pupil diameter. The TEPR latency was significantly delayed after participant watched a 3D video, but there was only a minute difference when the participants watched a 2D video. This was proved by the pupil diameter, which is functionally influenced by the brain processing such as cognitive load, perception, memory, attention, and brain activity. Previous studies have found the increase in the pupil diameter and pupil size change was strongly correlated with the degradation of the cognitive load. The pupillary response (pupil diameter) when the target was presented in participants each trials was processed by the grand average for all trials. The continuous pupillary response was dominated by grand average, and intermittent response was decayed. As mentioned before, the TEPR latency was related to the dominant location in the pupil size change after presented the target. Delaying of this response was related to degradation of the cognitive capacity of individuals for processing visual information, this finding was confirmed in this research.

In the MTMM analysis result, the HEP and TEPR measurements, comparing to other measurements, showed a high reliability in both 2D and 3D viewing test. These measurements also showed a strong reliability among repeated measures for the multi-method (2D and 3D viewing conditions). Generally, the electrophysiology measurements (ERP and HEP) showed higher reliability than the non-electrophysiology such as the response time and subjective rating. For the TEPR latency, there was an equivalent or more reliability compared with electrophysiology measures. These measures had a test re-test validity, where the HEP and TEPR measurement showed higher validity than the ERP measure. Correlation coefficients between HEP, ERP, and TEPR measurements showed a strong positive correlation. However, these measurements showed a low correlation coefficient in the response time and subjective rating. Thus, HEP, ERP, and TEPR measurements were shown to have the discriminant validity with non-electrophysiology measurements. These measurements, that is, has the same direction for evaluating the 3D visual (cognitive) fatigue.

Also, HEP and TEPR measurements were shown to have high convergent validity. The ERP and HEP has been well known as the indicator of the cognitive function related to the mental work load. In the TEPR latency, there was a low discriminant validity with ERP and HEP measures. In other words, the TEPR latency could be the measurement for the mental work load. Previous studies also proved that the pupillary response have the relationship with the cognitive function. The TEPR latency also holds the test-retest reliability and the convergent validity on par with HEP measure, higher than other measures. The results showed the superiority of TEPR latency, comparing to other measurements excluding the HEP, on the assessment of the 3D visual fatigue. Conclusively, the TEPR latency was recommended as better quantitative evaluators of the 3D visual fatigue than other measurements.

CONCLUSION

The purpose of this research was to evaluate a method for measuring the 3D cognitive fatigue based on the pupillary response (TEPR) overcoming measurement burden by using non-contact methods. The TEPR latency was showed a significantly delay when participants experienced the 3D cognitive fatigue. Other measurements such as subjective rating, response time, ERP latency, and HEP alpha power showed significance difference which was common with previous studies. From the outcome of the MTMM analysis, it was found that the TEPR latency and HEP alpha power has a strong reliability and high correlation with the 3D cognitive fatigue rather than other measurements. The research for the present invention found that the TEPR latency is useful for quantitatively determining the 3D visual fatigue. Therefore, because the TEPR latency can be easily evaluate the 3D visual fatigue by non-contact without measuring burdens, the proposed method provides the advantage of usability and eliminating all the disadvantages including the attachment burden, time wasting and time constraints according to the conventional sensor attachment.

According to present invention, causes of the 3D visual fatigue such as viewer characteristics, visual content, viewing environment, display, and device factors can be more easily determined by using a system adopting the method, based on a computer-architecture along with a video camera. Therefore, the method and system according to the present invention can be utilized to validate improvements in 3D technologies.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of measuring noncontact-vision-based cognitive fatigue, the method comprising;
    acquiring pupil images of a subject exposed to visual stimuli;
    extracting a task evoked pupillary response (TEPR) by using the pupil images;
    detecting dominant peaks from the TEPR;
    calculating latency of the dominant peaks; and
    determining cognitive fatigue of the subject by comparing a value of the latency to a predetermined reference value associated with cognitive fatigue.

2. The method of claim 1, wherein the acquiring of the pupil images comprises:
    capturing face images of the subject by using a video camera;
    extracting the pupil images from the face images; and
    extracting a pupil size variation (PSV) from the pupil images, and
    wherein the calculating comprises calculating the TEPR from the PSV.

3. The method of claim 2, wherein the extracting of the PSV comprises:
    resampling the face images at a predetermined frequency; and
    extracting the PSV from the resampled face images.

4. The method of claim 3, further comprising: extracting unit PSVs divided into epochs of 1200 ms based on a stimulus onset of −200 to 1000 milliseconds.

5. The method of claim 4, wherein the TEPR is calculated or produced by combining the unit PSVs by using a grand average technique.

6. A system for measuring noncontact-vision-based cognitive fatigue, the system comprising:
    a video camera configured to acquire pupil images of a subject exposed to visual stimuli;
    a processing unit configured to process the pupil images; and
    an analyzing unit configured to extract a task evoked pupillary response (TEPR) by using the pupil images, detect dominant peaks from the TEPR, calculate latency of the dominant peaks, and determine the cognitive fatigue by comparing a value of the latency to a predetermined reference value associated with cognitive fatigue.

7. The system of claim 6, wherein the processing unit is further configured to extract the pupil images from face images and extract a pupil size variation (PSV) from the pupil images by resampling at a predetermined sampling frequency.

8. The system of claim 7, wherein the analyzing unit is further configured to calculate unit PSVs divided into epochs of 1200 ms based on a stimulus onset of −200 to 1000 milliseconds.

9. The system of claim 8, wherein the analyzing unit is further configured to calculate the TEPR by combining the unit PSVs by using a grand average technique.

\* \* \* \* \*